United States Patent
Guo et al.

(10) Patent No.: US 10,456,033 B2
(45) Date of Patent: Oct. 29, 2019

(54) APPARATUS AND METHOD FOR MEASURING BLOOD FLOW OF VESSELS

(71) Applicant: SHENZHEN CERTAINN TECHNOLOGY CO., LTD., Shenzhen, Guangdong (CN)

(72) Inventors: Shuguang Guo, Guangdong (CN); Mingming Wan, Guangdong (CN); Peng Li, Guangdong (CN); Xiangsong Dai, Guangdong (CN); Dexing Zhang, Guangdong (CN)

(73) Assignee: SHENZHEN CERTAINN TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 15/574,934

(22) PCT Filed: Mar. 7, 2016

(86) PCT No.: PCT/CN2016/075790
§ 371 (c)(1),
(2) Date: Nov. 17, 2017

(87) PCT Pub. No.: WO2016/188178
PCT Pub. Date: Dec. 1, 2016

(65) Prior Publication Data
US 2018/0160901 A1    Jun. 14, 2018

(30) Foreign Application Priority Data
May 27, 2015    (CN) .................. 2015 1 02765642

(51) Int. Cl.
*A61B 3/12*    (2006.01)
*A61B 3/14*    (2006.01)
(Continued)

(52) U.S. Cl.
CPC ............ *A61B 3/1241* (2013.01); *A61B 3/102* (2013.01); *A61B 3/14* (2013.01); *A61B 5/0066* (2013.01);
(Continued)

(58) Field of Classification Search
CPC ....... A61B 3/00; A61B 3/0058; A61B 3/0025; A61B 3/0041; A61B 3/10; A61B 3/102;
(Continued)

(56) References Cited

U.S. PATENT DOCUMENTS

2007/0291277 A1    12/2007  Everett
2008/0097185 A1    4/2008   Feldman et al.
(Continued)

FOREIGN PATENT DOCUMENTS

CN    102438505    5/2012
CN    102525409    7/2012
(Continued)

OTHER PUBLICATIONS

International search report dated Apr. 20, 2016 from corresponding application No. PCT/CN2016/075790.
(Continued)

*Primary Examiner* — Jie Lei
(74) *Attorney, Agent, or Firm* — Hauptman Ham, LLP

(57) ABSTRACT

An apparatus and a method for measuring blood flow of vessels are provided. The apparatus includes a light source, a light splitting module, a reference arm module, a sample arm module, a probing module, and a control system. The sample arm module includes a scanning unit and an optical-path shifting device. A probe light is obtained from the light splitting module, and a central line of a main light of the probe light extends through a rotation axis of the scanning unit. The probe light is reflected by the scanning unit to the optical-path shifting device. When the optical-path shifting
(Continued)

device is rotated between a first position and a second position respectively, the probe light scans a vessel in fundus to obtain a first phase shift signal and a second phase shift signal blood flow rates and total blood flow of all the vessels near an optic disc are determined.

13 Claims, 10 Drawing Sheets

(51) Int. Cl.
    *G01B 9/02*     (2006.01)
    *A61B 5/00*     (2006.01)
    *A61B 3/10*     (2006.01)
    *A61B 5/026*     (2006.01)
    *G01N 21/47*     (2006.01)

(52) U.S. Cl.
    CPC .......... *A61B 5/0261* (2013.01); *A61B 5/7207* (2013.01); *G01B 9/0201* (2013.01); *G01B 9/0203* (2013.01); *G01B 9/02044* (2013.01); *G01B 9/02076* (2013.01); *G01B 9/02091* (2013.01); *G01N 21/4795* (2013.01)

(58) Field of Classification Search
    CPC ........... A61B 3/103; A61B 3/152; A61B 3/12; A61B 3/124; A61B 3/14; A61B 3/113; A61B 3/107; A61B 3/04; A61B 3/1225; A61B 3/1015; A61B 5/0066; A61B 5/0261; A61B 7/7207; G01B 9/0201; G01B 9/0203; G01B 9/02091; G01B 9/02044; G01B 9/02076; G01N 21/4795
    USPC ....... 351/206, 205, 208, 210, 212, 216, 221, 351/236, 246; 600/425, 476
    See application file for complete search history.

(56) References Cited

U.S. PATENT DOCUMENTS

| | | |
|---|---|---|
| 2009/0270738 A1 | 10/2009 | Izatt et al. |
| 2015/0092195 A1 | 4/2015 | Blatter et al. |
| 2016/0089025 A1* | 3/2016 | Huang ................ A61F 9/00736 351/221 |

FOREIGN PATENT DOCUMENTS

| | | |
|---|---|---|
| CN | 103002794 | 3/2013 |
| CN | 203885484 | 10/2014 |
| CN | 104159505 | 11/2014 |
| CN | 104168823 | 11/2014 |
| CN | 104825148 | 8/2015 |
| CN | 204708834 | 10/2015 |
| WO | 2015172322 A1 | 11/2015 |

OTHER PUBLICATIONS

The extended European search report dated Jan. 11, 2019 from corresponding application No. EP 16799067.0.

\* cited by examiner

APPARATUS AND METHOD FOR MEASURING BLOOD FLOW OF VESSELS

RELATED APPLICATIONS

The present application is a National Phase of International Application Number PCT/CN2016/075790, filed Mar. 7, 2016, and claims the priority of China Application No. 201510276564.2, filed May 27, 2015.

TECHNICAL FIELD

The present disclosure relates to the field of optoelectronic technology, and more particularly to an apparatus and method for measuring blood flow of vessels.

BACKGROUND

Many retinal diseases are related to abnormal eye blood flow, for example, retinopathy caused by diabetes, retinal vein occlusion, and age-related macular degeneration. In the study of glaucoma, insufficient blood supply to the retina is considered to be a possible reason of occurrence and development of glaucoma. Therefore, retinal blood flow measurement is important for the clinical diagnosis, treatment, and research of retinal diseases.

Optical coherence tomography (OCT) technology is a non-invasive detection technique, which is widely used in imaging of living cross-sectional structure of biological tissues. OCT can provide tissue structures with high resolution and high sensitivity by measuring a depth-related scattering light. At the same time, the OCT technology can also be used to detect Doppler shift of the scattering light to obtain motion information of a fluid and sample and therefore, it is suitable for measuring retinal blood flow. Unfortunately, the frequency shift probed by single-beam Doppler OCT only relates to the blood flow rate in the direction of the probe beam, and blood flow information in a direction perpendicular to the direction of the probe beam cannot be directly obtained from Doppler shift, therefore, it is impossible to obtain actual blood flow rate of vessels.

In order to solve the above problem, a series of techniques have been developed to obtain actual blood flow rate of the vessels.

(1) Through a three-dimension scanning of retina, directions in the space of vessels in the retina can be obtained, so as to determine a Doppler angle of a probe light, and then the Doppler angle can be used to calculate the actual blood flow rate. Because the vessels of the retina are almost perpendicular to probe beam, this method is less accurate. In addition, a space vector of a vessel to be measured is determined by continuously scanning two planes or rings and then the Doppler angle can be calculated to obtain the actual blood flow rate. But measurement results of this method can be affected by eye movement, and it can only measure the vessels around the optic disc and cannot measure blood flow in other areas of the retina.

(2) The same point in the sample can be scanned by using multi-beam and multi-angle probe light to obtain the actual blood flow rate of the vessels. The OCT probe light can be split into two beams by a glass plate, and the two light beams can converge in the fluid to form a dual-beam and dual-angle illumination mode. The actual blood flow rate of the vessels can be obtained by analyzing Doppler shift probed by the two light beams. The drawback of this method is that, due to the time delay between the two light beams, it is not applicable for a frequency domain OCT system. Furthermore, retina vessel blood flow and retina vessel blood flow rate can be measured by using a dual-beam OCT system with beams split by a polarized light, or a DOVE prism synchronized with a OCT scanning mechanism can be used to achieve dual-beam circular scanning of the retina. Those dual-beam systems consist of two Michelson interferometers, which are complex in structure and difficult to adjust, and taking into account the safety of probe light, the power of each probe light is much lower than that of a single-beam system, which reduces the sensitivity of the dual-beam OCT system, thereby increasing the phase noise of the system.

In order to measure the blood flow rate and blood flow of a single vessel and all vessels in the optic disc, fundus vessels must be scanned by ophthalmic diagnostic equipment. Please refer to FIG. 3, FIG. 10, and FIG. 11, in which FIG. 3 is a video screenshot of linear scanning of one vessel in the optic disc, and FIGS. 10-11 are schematic diagram illustrating circular scanning of all vessels in the optic disc. As illustrated in FIG. 3, a black bond line indicates a scanning direction that the probe light scans a fundus vessel B, and the scanning direction corresponds to Y-axis direction illustrated in FIG. 9. After scanning by the probe light, an original fundus Doppler image may be obtained as illustrated in FIG. 4. In FIG. 4, there is undesired background Doppler (namely low-frequency background Doppler with alternate dark) and bright and high-frequency background Doppler with obvious vertical lines. Similarly, in the process of circular scanning of all the vessels in the optic disc as illustrated in FIGS. 10-11, an original Doppler image obtained (not illustrated) also has low-frequency background Doppler with alternate dark and bright and high-frequency background Doppler with obvious vertical lines as shown in FIG. 4. After analysis, there are two reasons for generating the background Doppler. First, a central line of a main light of the probe light does not extend through a rotation axis of a scanning unit. When the scanning unit is an X-Y galvanometer, it can be considered that a rotation axis of a Y galvanometer is the rotation axis of the scanning unit. Referring to FIG. 1, when the scanning unit is the X-Y galvanometer, if a central line O1 of the main light of the probe light extends through a rotation axis 902 of an X-Y galvanometer 900, then it is considered that the central line O1 of the main light of the probe light extends through the rotation axis of the scanning unit. With the swing of the X-Y galvanometer 900, an incidence direction e of the probe light is perpendicular to the scanning direction of the probe light on an imaging plane d of a lens 1, in this case, no additional background Doppler is introduced. Referring to FIG. 2, if the central line O1 of the main light of the probe light does not extend through the rotation axis 902 of the X-Y galvanometer 900, with the swing of the X-Y galvanometer, the incidence direction e of the probe light is no longer perpendicular to the scanning direction of the probe light on the imaging plane d of the lens 1. If an incident light deviates from a rotation axis of a galvanometer, scanning angular rate of the galvanometer is denoted by w, and focal length of the lens 1 is denoted by f, and then a frequency shift F obtained can be expressed as: $F=2\,fwL/\lambda_0\sqrt{L^2+f^2}$, where $\lambda_0$ represents a center wavelength of the probe light. High-frequency background Doppler can be removed by removing lines one by one in vertical, and it is easy to get a wrong background, which may directly affect accuracy of measurement. Second, in the process of detecting eyes, eyeballs will be involuntary rotate slightly, and thus the probe light cannot be always incident on a same position of the eyeball at a same angle, which can lead to region-shaped low-frequency background Doppler with alternate dark and bright as illustrated in FIG. 4.

Low-frequency background Doppler can be easily removed by well-known methods for removing Doppler background. For high-frequency background Doppler, because the background between each two adjacent lines is different and irregular, it is necessary to find out background Doppler for each line. This not only makes the process of removing background more tedious, but also different to ensure the accuracy rate of removing background. Wrong removal of the background will directly affect the accuracy of measuring blood flow rate of vessels, and it is necessary to remove high-frequency background Doppler by adjusting the optical path.

SUMMARY

In view of the deficiencies in the related art, the disclosure provides an apparatus and a method which can eliminate high-frequency background Doppler and measure blood flow of vessels of an optic disc accurately.

Technique solutions of the apparatus for measuring blood flow of the vessels are disclosed by this disclosure as follows.

An apparatus for measuring blood flow of vessels may include a light source, a light splitting module, a reference arm module, a sample arm module, a probing module, and a control system. Light emitted by the light source is split by the light splitting module to form a reference light and a probe light. The reference light is incident to the reference arm module, and the probe light is incident to the sample arm module. The sample arm module may include a scanning unit and a rotatable optical-path shifting device, and a central line of a main light of the probe light extends through a rotation axis of the scanning unit.

When the optical-path shifting device is in a first position, the probe light is configured to be reflected by the scanning unit to enter the optical-path shifting device, to scan a vessel in a first direction and carry information of the vessel scanned after passing through the optical-path shifting device, to be returned by the sample arm module, and to interfere at the light splitting module with the reference light returned from the reference arm module to generate a first interference light. The first interference light is configured to be probed by the probing module and then processed by the control system to obtain a first phase shift signal of the vessel.

When the optical-path shifting device is in a second position, the probe light is configured to be reflected by the scanning unit to enter the optical-path shifting device, to scan the vessel in a second direction and carry information of the vessel scanned after then the probe light passing through the optical-path shifting device, to be returned by the sample arm module, and to interfere with the reference light returned from the reference arm module at the light splitting module to generate a second interference light. The second interference light is configured to be probed by the probing module and then processed by the control system to obtain a second phase shift signal of the vessel.

A line extending through a point where the main light of the probe light irradiates on the scanning unit and a point where the main light of the probe light irradiates on the optical-path shifting device is collinear with a rotation axis of the optical-path shifting device.

Further, the angle of rotation is 180° when the optical-path shifting device is rotated from the first position to the second position.

The sample arm module may further include a collimating mirror, a relay lens, a dichroic mirror, and an ophthalmoscope. The collimating mirror is configured to collimate the probe light obtained after splitting by the light splitting module. The relay lens is configured to converge the probe light from the optical-path shifting device on the dichroic mirror. The dichroic mirror is configured to reflect the probe light from the relay lens to the ophthalmoscope to be converged to scan vessels.

Further, the sample arm module includes a preview module including a illumination light source, a first lens, and a camera. Light emitted by the illumination light source irradiates into eyes and then reflects in fundus. The light reflected is then sequentially transmitted by the ophthalmoscope, the dichroic mirror, and the first lens, and then is received by the camera and displayed by a computer.

Further, the scanning unit is an X-Y galvanometer, and a rotation axis of the scanning unit is a rotation axis of the X-Y galvanometer.

The optical-path shifting device is at least one of a plate glass having two chamfered ends, two speculums arranged in parallel, or a prism.

According to embodiments of the present disclosure, there is provided a method for measuring blood flow of a single-vessel, which includes the following steps.

A light source, a probing module, a light splitting module, a reference arm module, a sample arm module, and a control system are arranged according to an optical path. The sample arm module includes a scanning unit and a rotatable optical-path shifting device. A central line of a main light of a probe light obtained from the light source after splitting extends through a rotation axis of the scanning unit.

When the optical-path shifting device is in a first position, the probe light is configured to be reflected by the scanning unit to enter the optical-path shifting device, to scan a vessel in a first direction and generate a first phase shift signal after passing through the optical-path shifting device.

When the optical-path shifting device is in a second position, the probe light is configured to be reflected by the scanning unit to enter the optical-path shifting device, to scan the vessel in a second direction and generate a second phase shift signal after passing through the optical-path shifting device.

Blood flow of the vessel is calculated according to the first phase shift signal and the second phase shift signal.

Further, after the probe light scans the vessel in the second direction and generates the second phase shift signal, the second phase shift signal can be modified, which can be implemented as follows.

A relationship of the first phase shift signal and the second phase shift signal over time is obtained. The second phase shift signal is modified by using interpolation calculation.

Before blood flow of the vessel measured is calculated according to the first phase shift signal and the second phase shift signal, the method may further include the following.

An angle between an axial direction of the vessel and an X-axis direction is measured.

When the optical-path shifting device is in the first position, the probe light is configured to scan the vessel in the first direction; when the optical-path shifting device is in the second position, the probe light is configured to scan the vessel in the second direction, and the first direction and the second direction constitute an X-Z plane.

According to this disclosure, there is further disclosed a method for measuring total blood flow of vessels near an optic disc, which includes the following steps.

A light source, a probing module, a light splitting module, a reference arm module, a sample arm module, and a control system are arranged according to an optical path. The sample arm module may include a scanning unit and a rotatable optical-path shifting device. Light emitted by the light source is split by the light splitting module to obtain a probe light, and the probe light has a main light, and a central line of the main light extends through a rotation axis of the scanning unit.

When the optical-path shifting device is in a first position, the probe light is configured to be reflected by the scanning unit to the optical-path shifting device; after the scanning unit and the optical-path shifting device rotate synchronously under the control of the control system, the probe light is configured to circularly scan all vessels near the optic disc in a first direction, to obtain a plurality of first phase shift signals that are in one-to-one correspondence with the vessels.

When the optical-path shifting device is in a second position, the probe light is configured to be reflected by the scanning unit to the optical-path shifting device; after the scanning unit and the optical-path shifting device rotate synchronously under the control of the control system, the probe light is configured to circularly scan the vessels near the optic disc in a second direction, to obtain a plurality of second phase shift signals modified, that are in one-to-one correspondence with the vessels.

The plurality of first phase shift signals and the plurality of second phase shift signals are matched and calculated one by one, to obtain multiple blood flow rates corresponding to multiple vessels.

Absolute values of the plurality of single-vessels blood flow rates are calculated to obtain blood flow of the vessels near the optic disc.

A scanning trajectory when the probe light scans in the second direction is the same as in the first direction.

The apparatus and the method according to the disclosure may have the following advantageous effects.

First, when the blood flow rate and blood flow of any single-vessel near the optic disc are measured and the central line of the main light of the probe light extends through the rotation axis of the scanning unit, the probe light is reflected to the optical-path shifting device by the scanning unit. When the optical-path shifting device is in the first position, the probe light is configured to scan a vessel B in a first direction S1 and along a Y-axis direction after passing through the optical-path shifting device, and the system obtains the first phase shift signal of the vessel. When the optical-path shifting device is in the second position, the probe light is configured to scan the vessel B in a second direction S2 and along the Y-axis direction, and then the system obtains the second phase shift signal of the vessel B. The system processes the first phase shift signal and the second phase shift signal to obtain the blood flow rate of the vessel B after calculating, and then blood flow of the vessel B can be obtained. The central line of the main light of the probe light extends through the rotation axis of the scanning unit, the probe light is reflected by the scanning unit to enter the optical-path shifting device to scan fundus vessels, therefore, regardless of whether the optical-path shifting device is in the first position or in the second position, the central line of the main light of the probe light always extends through the rotation axis of the scanning unit when the scanning unit scans the vessels, which effectively avoiding high-frequency background Doppler appearing in an original fundus Doppler image illustrated in FIG. 4, so that extra work and error caused by removing high-frequency background Doppler can be eliminated.

Second, when blood flow of all the vessels near the optic disc is measured and the central line of the main light of the probe light extends through the rotation axis of the scanning unit as well, the probe light is reflected by the scanning unit to the optical-path shifting device, after the control system controls the scanning unit and the optical-path shifting device to rotate synchronously, the probe light circularly scans the vessels near the optic disc in the first direction S1 and the second direction S2 respectively. Similarly, the central line of the main light of the probe light extends through the rotation axis of the scanning unit, as such the original fundus Doppler image obtained by scanning the vessels near the optic disc circularly will not be accompanied by high-frequency background Doppler illustrated in FIG. 4, and extra work and error caused by removing high-frequency background Doppler can be eliminated.

Figure 1:
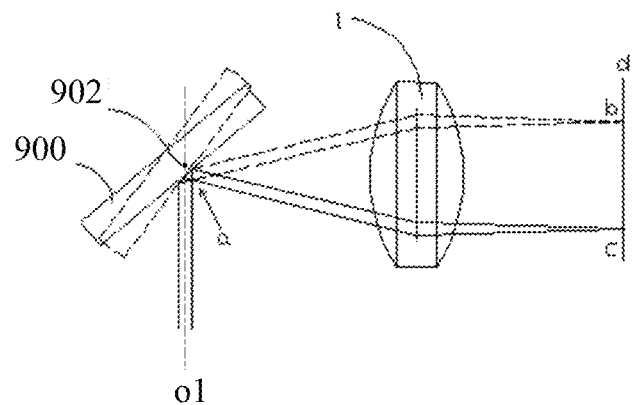
FIG. 1 is a schematic diagram in which a central line of a main light of a probe light extends through a rotation axis of a scanning unit.
Figure 2:
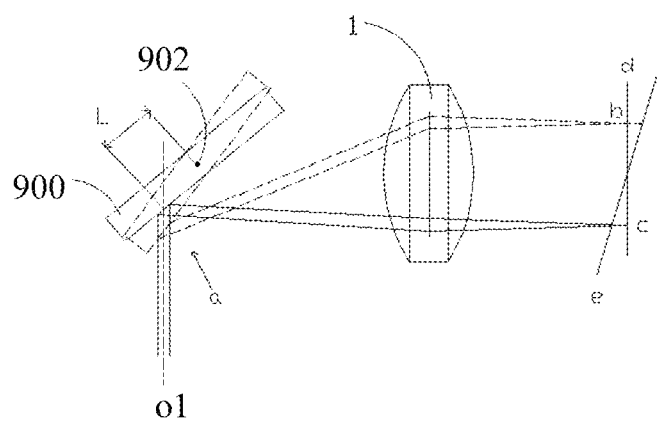
FIG. 2 is a schematic diagram in which a central line of a main light of a probe light deviates from a rotation axis of a scanning unit.
Figure 3:
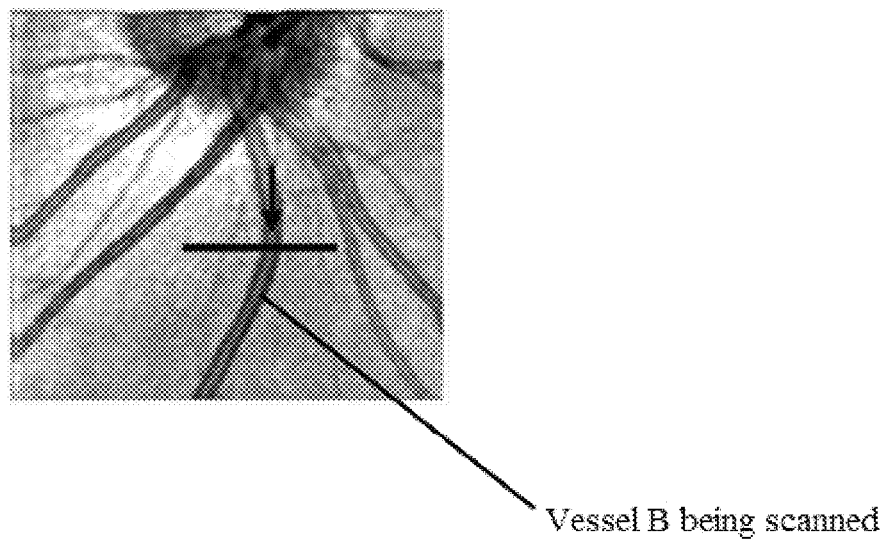
FIG. 3 is a video screenshot in which a probe light is configured to scan one vessel B in fundus.

REFERRAL NUMBERS IN THE FIGURES 1. lens
100. light source
200. light splitting module
300. reference arm module
301. reference mirror
400. collimating mirror
50. main light of a probe light
500. sample arm module
501. scanning unit
900. X-Y galvanometer
902. rotation axis
502. optical-path shifting device
502C. rotation axis of the optical-path shifting device 502
502A. incident surface of a first structure of the optical-path shifting device 502
502B. emergent surface of the first structure of the optical-path shifting device 502
502D. first speculum of a second structure of the optical-path shifting device 502
502E. second speculum of the second structure of the optical-path shifting device 502
502F. first reflective surface of a third structure of the optical-path shifting device 502
502G. second reflective surface of the third structure of the optical-path shifting device 502
503. dichroic mirror
504. ophthalmoscope
505. preview module
505A. first lens
505B. camera
600. probing module
506. relay lens
700. control system
800. eye

DETAILED DESCRIPTION OF ILLUSTRATED EMBODIMENTS

In order to better illustrate technical problems to be solved, technical solutions, and advantageous effects of the present disclosure more clearly, a further description of the embodiments and accompanying drawings used herein are given below. Obviously, the embodiments described below are merely examples and the scope of the disclosure is not limited thereto.

An apparatus for measuring blood flow of vessels is provided. The apparatus is configured to measure blood flow of tissues and organs of humans, the phrase "tissues and organs" includes, but not limited to, eyes of humans or animals. In accompanying drawings of the present disclosure, a vessel of an eye is described as an example of an object of measurement, however, the apparatus and method are also applicable to the measurement of blood flow of tissues and organs other than the eyes of the humans and animals, in which case the "eye" or graphical representation thereof illustrated in the embodiments or the figures should be replaced with other tissues and organs correspondingly. Similarly, "sample" described herein blow may include, but not limited to, eyes of humans or animals; alternatively, the "sample" can be replaced with other tissues or organs of humans or animals.

Figure 6:
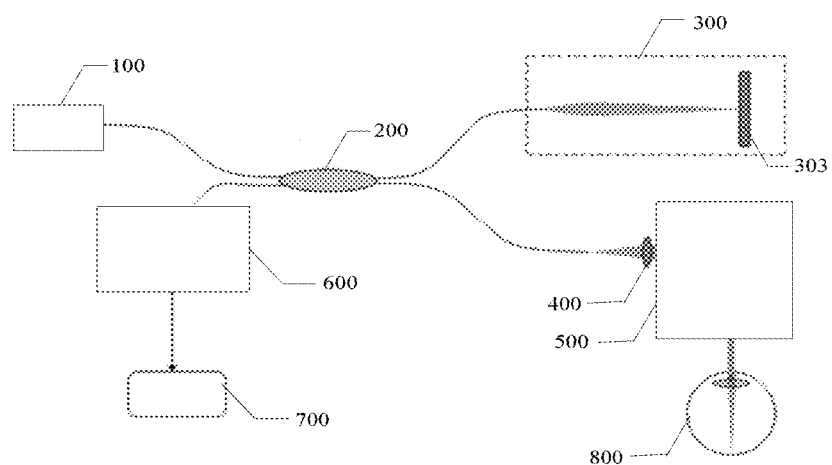
FIG. 6 is a schematic structural diagram illustrating an apparatus for measuring blood flow of a vessel according to an embodiment of the disclosure.

Referring to FIG. 6, an apparatus for measuring blood flow can eliminate high-frequency background Doppler and includes a light source 100, a light splitting module 200, a reference arm module 300, a sample arm module 500, a probing module 600, and a control system 700. Light emitted by the light source 100 passes through the light splitting module 200, and the light splitting module 200 splits light received into a reference light and a probe light. The reference light is transferred to the reference arm module 300. The probe light is transferred to the sample arm module 500. The reference light received by the reference arm module 300 is returned to the light splitting module 200 after reflection. The probe light is collimated by a collimating mirror 400 to pass through the sample arm module 500 and then scan an eye 800; the probe light is then scattered in tissues of the eye 800 to form a signal light, and return to the light splitting module 200 by the collimating mirror 400 again. The signal light interferes with the reference light at the light splitting module 200 to form an interference light. The probing module 600 receives the interference light and then transmits a signal carried by the interference light to the control system 700. The signal will be processed by the control system 700 to obtain a phase shift signal of the tissues of the eye scanned. Furthermore, a reference mirror 301 is built into the reference arm module 300, and the reference light obtained by splitting of the light splitting module 200 is reflected by the reference mirror 301 and return to the light splitting module 200, where the reference light interferes with the signal light. For example, the reference mirror 301 may be a plane mirror. The control system 700 referred to herein may be a processing module of a computer.

Referring to FIGS. 7-12, the sample arm module 500 may at least include a scanning unit 501 and an optical-path shifting device 502. A main light 50 of the probe light is obtained by splitting of the light splitting module 200. A central line of the main light 50 extends through the rotation axis of the scanning unit 501. The scanning unit may be an X-Y galvanometer. As illustrated in FIGS. 7-12, the central line of the main light of the probe light always extends through the rotation axis of the scanning unit 501.

FIGS. 7-12 illustrate optical-path structures of the sample arm module 500 of an optical-path shifting device 502 according to three embodiments. It should be noted that, the three embodiments are merely exemplary embodiments, and the optical-path structures are for the purpose of shifting a main light 50 of the probe light, when the probe light irradiates to the optical-path shifting device 502 and exits from the optical-path shifting device 502. The optical-path shifting device 502 is rotated about a rotation axis to be in a first position and in a second position. A line extending through a point where the main light 50 of the probe light irradiates on the scanning unit 501 and a point where the main light 50 of the probe light irradiates on the optical-path shifting device 502 is collinear with the rotation axis 502C of the optical-path shifting device 502. Therefore, other optical-path structures that can achieve the function shall fall in the protection scope of the disclosure.

In a first embodiment, the optical-path shifting device 502 is a glass plate having two chamfered ends.

Figure 7:
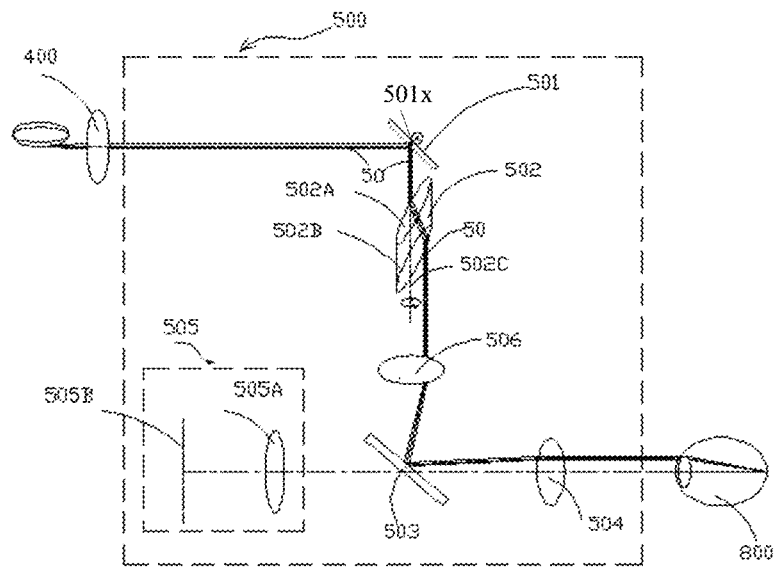
FIG. 7 illustrates an optical-path diagram when a first structure of an optical-path shifting device 502 of a sample arm module 500 illustrated in FIG. 6 is in a first position.
Figure 13:
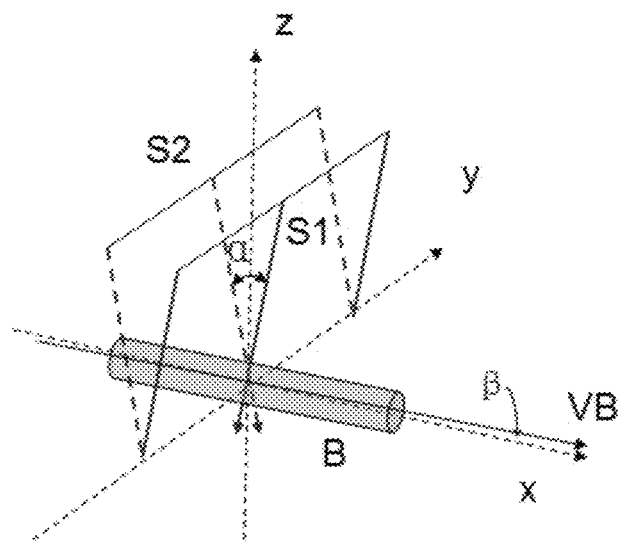
FIG. 13 is a schematic diagram illustrating geometric space consisting of an angle α formed when probe light incidents on the retina of the eye and an vessel B, when the optical-path shifting device 502 is in a first position and a second position.

Referring to FIG. 7, when a blood flow rate of a vessel B is measured and the optical-path shifting device 502 is in a first position, a central line of the main light 50 of the probe light extends through a rotation axis 501x of the scanning unit 501. The probe light is reflected to the optical-path shifting device 502 by the scanning unit 501, and refracted at an incident surface 502A of the optical-path shifting device 502. Thereafter, the probe light is refracted again by an emergent surface 502B of the optical-path shifting device 502. Then the probe light will scan the vessel B (as illustrated in FIG. 13) of the eye 800 in a first direction S1 and along a Y-axis direction. After scanning, the probe light carrying a signal of the vessel B will be scattered in fundus, and return to the light splitting module 200 as illustrated in FIG. 6 according to the original path. The probe light then interferes with the reference light returned from the reference arm module 300 at the light splitting module 200 to form a first interference light. The first interference light is probed by the probing module 600 and a first phase shift signal $\Phi_a$ of the vessel B scanned is obtained by the system. In FIG. 7, the central line of the main light 50 of the probe light reflected from the scanning unit 501 to the incident surface 502A of the optical-path shifting device 502 is collinear with the rotation axis 502C of the optical-path shifting device 502.

Figure 8:
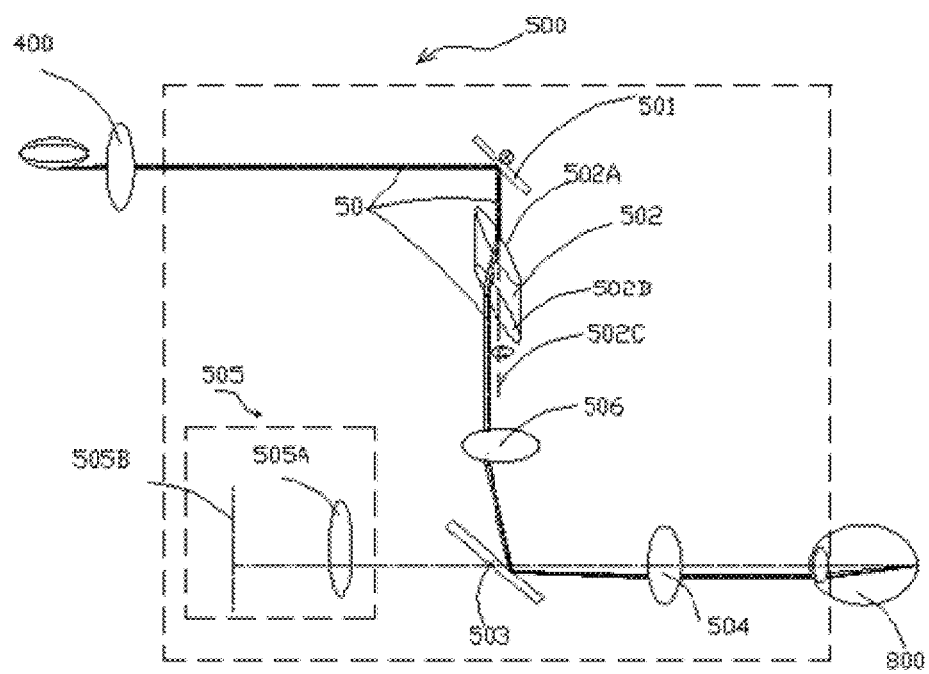
FIG. 8 illustrates an optical-path diagram when the first structure of the optical-path shifting device 502 of the sample arm module 500 illustrated in FIG. 6 is in a second position, compared with FIG. 7, an angle of rotation of the optical-path shifting device 502 is 180°.
Figure 9:
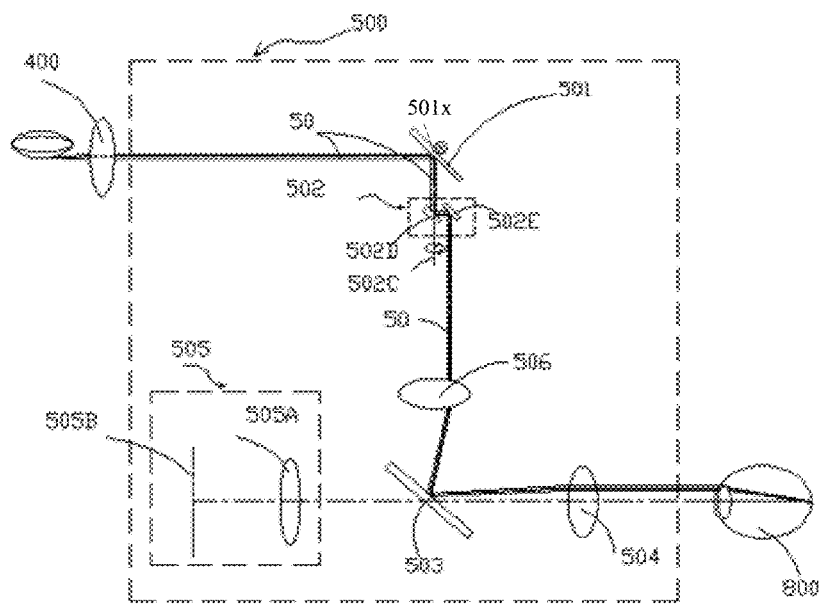
FIG. 9 illustrates an optical-path diagram when a second structure of the optical-path shifting device 502 of the sample arm module 500 illustrated in FIG. 6 is in a first position.

Referring to FIG. 8, when the optical-path shifting device 502 is rotated 180° to a second position as illustrated in FIG. 8, the central line of the main light 50 of the probe light extends through the rotation axis 501x of the scanning unit 501. The probe light is reflected to the optical-path shifting device 502 by the scanning unit 501, and refracted at an incident surface 502A of the optical-path shifting device 502. Thereafter, the probe light is refracted again by an emergent surface 502B of the optical-path shifting device 502. Referring to FIG. 9, the probe light will scan the vessel B in a second direction S2 and along the Y-axis direction. Then the probe light carrying a second signal of the vessel B will be scattered in fundus, and returns to the light splitting module 200 illustrated in FIG. 6 according to the original path. The probe light then interferes with the reference light returned from the reference arm module 300 at the light splitting module 200 to generate a second interference light. The second interference light is probed by the probing module 600 to obtain a second phase shift signal $\Phi_b$ of the vessel scanned. It should be understood that, in FIG. 8, the central line of the main light 50 of the probe light reflected from the scanning unit 501 to the emergent surface 502B of the optical-path shifting device 502 is collinear with the rotation axis 502C of the optical-path shifting device 502.

In a second embodiment, the optical-path shifting device 502 is two speculums arranged in parallel.

Figure 10:
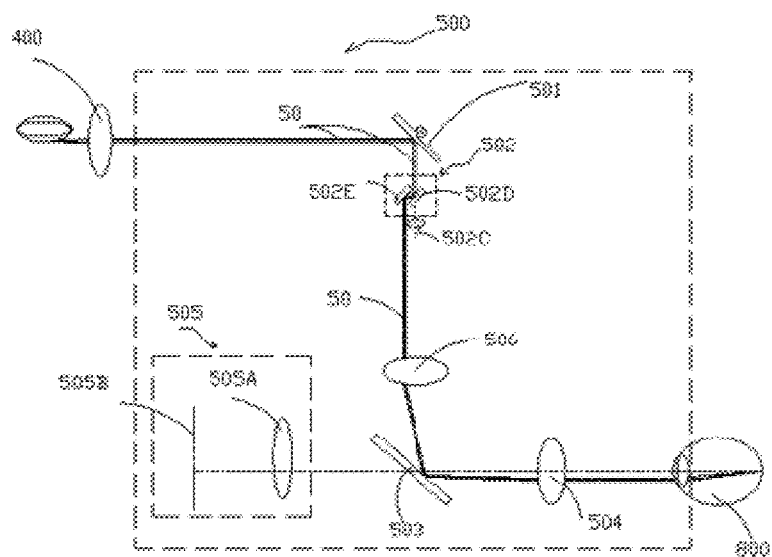
FIG. 10 illustrates an optical-path diagram when a second structure of the optical-path shifting device 502 of the sample arm module 500 illustrated in FIG. 6 is in a second position, compared with FIG. 9, an angle of rotation of the optical-path shifting device 502 is 180°.

Referring to FIGS. 9-10, different from the first embodiment, the optical-path shifting device 502 in the second embodiment includes a first speculum 502D and a second speculum 502E that are arranged in parallel. Referring to FIG. 9, when the optical-path shifting device 502 is in a first position, the central line of the main light 50 of the probe light extends through the rotation axis 501x of the scanning unit 501. The probe light is reflected to the optical-path shifting device 502 by the scanning unit, reflected to the second speculum 502E by the first speculum 502D, and emerged from the second speculum 502E. Then the probe light will scan the vessel B (illustrated in FIG. 13) of the eye 800 in a first direction S1 and along a Y-axis direction. After scanning, the probe light carrying a signal of the vessel B will be scatted in fundus, and return to the light splitting module 200 illustrated in FIG. 6 according to the original path. The probe light then interferes with the reference light returned from the reference arm module 300 at the light splitting module 200 to form a first interference light. The first interference light is probed by the probing module 600 and a first phase shift signal $\Phi_a$ of the vessel B scanned is obtained by the system. In FIG. 9, the central line of the main light 50 of the probe light reflected from the scanning unit 501 to the first speculum 502D is collinear with the rotation axis 502C of the optical-path shifting device 502.

Referring to FIG. 10, when the optical-path shifting device 502 is in a second position, at this time, the first speculum 502D and the second speculum 502E are as a whole to rotate 180° along the rotation axis 502C. The central line of the main light 50 of the probe light extends through the rotating axis 501x of the scanning unit 501. The probe light is reflected to the optical-path shifting device 502 by the scanning unit 501, reflected to the first speculum 502D by the second speculum 502E, and emerged from the first speculum 502D. At last, the probe light will scan the vessel B of the eye 800 in the second direction S2 and along the Y-axis direction. After scanning, the probe light carrying a signal of the vessel B will be scattered in fundus, and return to the light splitting module 200 illustrated in FIG. 6 according to the original path. The probe light then interferes with the reference light returned from the reference arm module 300 to form a second interference light at the light splitting module 200. The second interference light is probed by the probing module 600, and the system obtains a second phase shift signal $\Phi_b$ of the vessel B scanned. It should be understood that, in FIG. 10, the central line of the main light 50 of the probe light reflected to the first speculum 502D from the scanning unit 501 is collinear with the rotation axis 502C of the optical-path shifting device 502.

In a third embodiment, the optical-path shifting device 502 is a prism.

Figure 11:
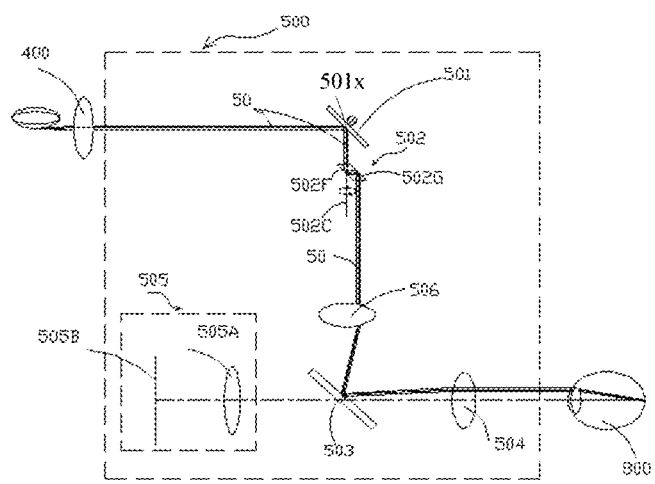
FIG. 11 illustrates an optical-path diagram when a third structure of the optical-path shifting device 502 of the sample arm module 500 illustrated in FIG. 6 is in a first position.

Referring to FIG. 11, when the optical-path shifting device 502 is in a first position, the central line of the main light 50 of the probe light extends through the rotation axis 501x of the scanning unit 501. The probe light is reflected to the optical-path shifting device 502 by the scanning unit 501. At this moment, the optical-path shifting device 502 is a prism. The probe light is reflected to a second reflective surface 502G of the prism by a first reflective surface 502F of the prism, and emerged from the second reflective surface 502G. Then the probe light will scan the vessel B of the eye 800 in a first direction S1 and along a Y-axis direction. After scanning, the probe light carrying a signal of the vessel B will be scattered in fundus, and return to the light splitting module 200 illustrated in FIG. 6 according to the original path. The probe light then interferes with the reference light returned from the reference arm module 300 at the light splitting module 200 to form a first interference light. The first interference light is probed by the probing module 600 to obtain a first phase shift signal $\Phi_a$ of the vessel B scanned. It should be understood that, in FIG. 11, the central line of the main light 50 of the probe light reflected to the first reflective surface 502F from the scanning unit 501 is collinear with the rotation axis 502C.

Figure 12:
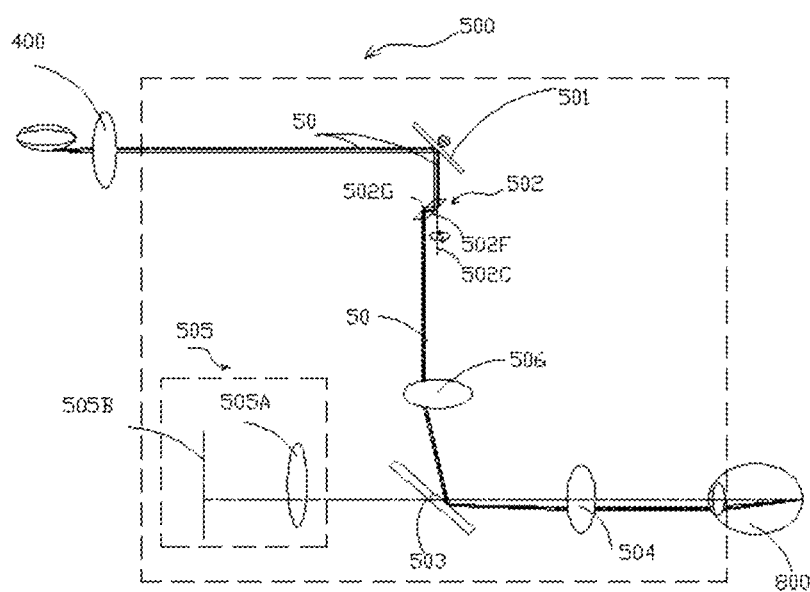
FIG. 12 illustrates an optical-path diagram when a third structure of the optical-path shifting device 502 of the sample arm module 500 illustrated in FIG. 6 is in a second position, compared with FIG. 11, an angle of rotation of the optical-path shifting device 502 is 180°.

Referring to FIG. 12, when the optical-path shifting device 502 is in a second position, that is, the prism is rotated 180° along with the rotation axis 502C, and the central line of the main light 50 of the probe light extends through the rotation axis 501x of the scanning unit 501. The probe light is reflected to the optical-path shifting device 502 by the scanning unit 501, reflected to the first reflective surface 502F by the second reflective surface 502G of the prism, and emerged from the first reflective surface 502F. Thereafter, the probe light will scan the vessel B of the eye 800 in a second direction S2 and along a Y-axis direction. After scanning, the probe light carrying a signal of the vessel B will be reflected in fundus and return to the light splitting module 200 illustrated in FIG. 6 according to the original path. The probe light then interferes with the reference light returned from the reference arm module 300 to form a second interference light at the light splitting module 200. The second interference light is probed by the probing module 600 to obtain a second phase shift signal $\Phi_b$ of the vessel B scanned. It needs to be understood that, in FIG. 12, the central line of the main light 50 of the probe light reflected to the first reflective surface 502F from the scanning unit 501 is collinear with the rotation axis 502C.

Referring to FIG. 13, an angle between the first direction S1 and the second direction S2 is defined as α, and the first direction S1 and the second direction S2 constitute an X-Z plane. When the first phase shift signal $\Phi_a$ and the second phase shift signal $\Phi_b$ are determined, the blood flow rate V of the vessel B to be measured can be calculated according to Formula (1).

$$v = \frac{(\phi_a - \phi_b)\lambda_0}{4\pi n \tau \alpha \cos\beta} \quad (1)$$

In Formula (1), $\lambda_0$ represents a central wavelength of the probe light, n represents a blood rate of the vessel B illustrated in FIG. 13; z represents a time interval of scanning between two adjacent lights of the OCT system; β is an angle between a blood flow direction VB of the vessel B and the X-Z plane, and can be obtained from a three-dimension projection diagram of the retina. For example, a three-dimension scanning may be implemented along the X-axis direction when the probe light is incident into the vessel B in the first direction S1, and in a synthetic fundus plan view, an angle between the vessel B and the X-axis direction is angle β. When parameters mentioned above are determined, the blood flow rate V of the vessel B to be measured in the retina of the eye 800 will be determined according to Formula (1). Thus, the blood flow rate of any single-vessel at any time in the retina of the eye 800 can be calculated according to Formula (1).

It will be appreciated that, in embodiments of the disclosure, according to directions and distributions in the space of the vessel B, the probe light and the scanning unit 501 can cooperate with each other to scan in various directions, such as an X-axis direction scanning, a Y-axis direction scanning, or a slant scanning etc., so that the probe light can adjust a scanning direction based on an actual direction in the space of the vessel B to be measured.

Referring to FIG. 7 to FIG. 12, as a further improvement, the sample arm module 500 further includes a collimating mirror 400, a dichroic mirror 503, an ophthalmoscope 504, and a relay lens 506. The collimating mirror 400 is disposed between the light splitting module 200 and the scanning unit 501, and configured to collimate the reference light incident to the scanning unit 501. The relay lens 506 is configured to converge the probe light from the optical-path shifting device 502 on the dichroic mirror 503. The dichroic mirror 503 is configured to reflect the probe light from the relay lens 506 to the ophthalmoscope 504 to be transmitted incident to the eye 800. After reflected in fundus, the probe light carrying information of the vessel scanned returns to the light splitting module 200 illustrated in FIG. 6 according to the original path.

Further, referring to FIG. 7 to FIG. 12, the apparatus of the disclosure further includes a preview module 50. The preview module 505 may include an illumination light source (not illustrated), a first lens 505A, and a camera 505B. Light emitted by the illumination light source irradiates into eyes, and then is reflected in the eye 800. The light reflected is then transmitted by the ophthalmoscope 504, the dichroic mirror 503, and the first lens 505A sequentially to reach the camera 505B. Information of the reflected light is captured by the camera 505B. Images captured by the camera 505B are displayed on a display screen of the control system 700, which will facilitate an operator to know relevant information of the eye 800 for further operation.

In this apparatus, the central line of the main light of the probe light always extends through the rotation axis of the scanning unit, and the probe light is reflected by the scanning unit 501 to the optical-path shifting device 502. That is, when the optical-path shifting device 502 is in a first position and a second position respectively, the central line of the main light of the probe light always extends through the rotation axis 501x of the scanning unit 501. In other words, the central line of the main light of the probe light will not deviate from the rotation axis 501x of the scanning unit 501 due to rotation of the optical-path shifting device 502. Therefore, undesired high-frequency background Doppler appearing in an original Doppler image of the vessel B measured illustrated in FIG. 4 can be avoided, and the original Doppler image of the vessel B illustrated in FIG. 5 can be directly obtained, and the blood flow rate of the vessel B measured can be determined according to Formula (1). The apparatus avoids extra work and error due to unable to remove high-frequency background Doppler properly.

It should be noted that, the vessel B is one of the vessels of the eye 800 of an optic disc, and it is exemplary. When vessels of other tissues in samples are scanned by the apparatus, background Doppler appearing in the original Doppler image of the vessels B can be eliminated as well.

Figure 17:
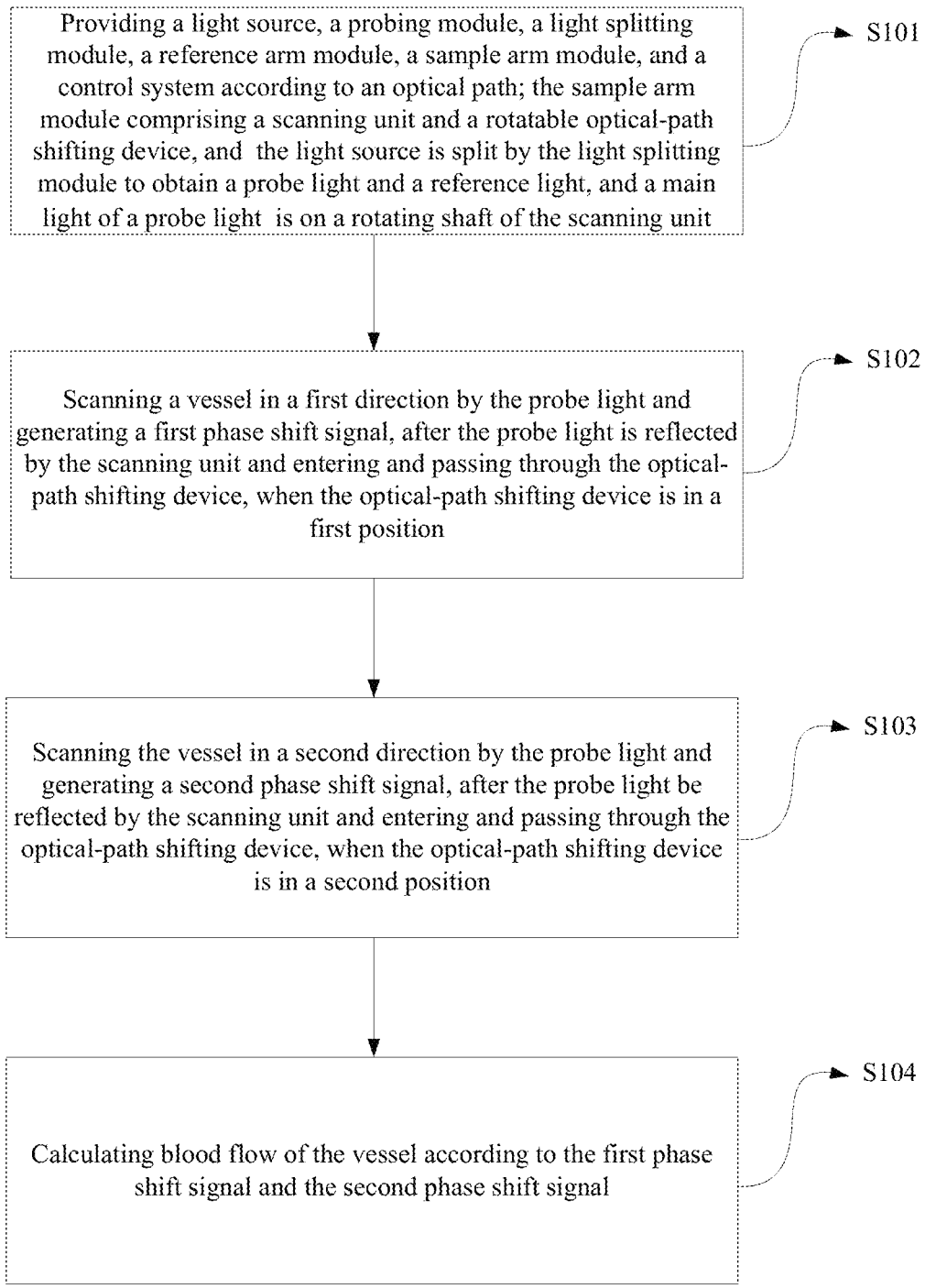
FIG. 17 is a flow chart illustrating a method for measuring blood flow of a single-vessel near an optic disc with eliminating high-frequency background Doppler.

Referring to FIG. 17, a method for measuring blood flow of vessels is provided by the disclosure. The method may include the following.

At S101, a light source, a probing module, a light splitting module, a reference arm module, a sample arm module, and a control system are arranged according to an optical-path; the sample arm module includes a scanning unit and a rotatable optical-path shifting device; Light emitted by the light source is split by the light splitting module to obtain a probe light and a reference light, and a central line of a main light of the probe light extends through a rotation axis of the scanning unit.

At S102, when the optical-path shifting device is in a first position, the probe light is reflected by the scanning unit to enter the optical-path shifting device, and to scan a vessel in a first direction and generate a first phase shift signal.

At S103, when the optical-path shifting device is in a second position, the probe light is reflected by the scanning unit to enter the optical-path shifting device, and to scan the vessel in a second direction and generate a second phase shift signal.

At S104, blood flow of the vessel is calculated according to the first phase shift signal and the second phase shift signal.

S101-S104 will be described below in detail.

For S101, first, a light source 100, a light splitting module 200, a reference arm module 300, a sample arm module 500, a probing module 600, and a control system 700 are set sequentially in accordance with FIG. 6. Light emitted by the light source 100 passes through the light splitting module 200 and then is split into two beams, namely a reference light and a probe light. The reference light is incident to the reference arm module 300. The probe light is incident to the sample arm module 500. The reference light received by the reference arm module 300 is configured to be returned to the light splitting module 200 after reflection. The probe light is configured to be incident into an eye 800 to scan the vessel after passing through the sample arm module 500. The probe light carrying information of the vessel is scattered in fundus of the eye 800, and then returns to the light splitting module 200. The probe light returned and carrying information of the vessel interferes with the reference light at the light splitting module 200 to generate an interference light. The probing module 600 receives the interference light and transmits the same to the control system 700. The interference light will be processed by the control system 700 to obtain a phase shift signal of the vessel scanned.

Referring to FIGS. 7-12, the sample arm module 500 may at least include a scanning unit 501 and an optical-path shifting device 502 as mentioned earlier. The optical-path shifting device 502 is rotatable about a rotation axis 502C. The optical-path shifting device 502 may be driven to rotate by a motor or other mechanical structure. When a central line of the main light of the probe light extends through a rotation axis 501x of the scanning unit 501, the central line of the main light 50 of the probe light will always extend through the rotation axis 501x of the scanning unit 501 regardless of whether the optical-path shifting device 502 is in the first position or in the second position after a 180° rotation. As such, the original Doppler image obtained by scanning a single-vessel with the apparatus of the present disclosure will not be accompanied by the high-frequency background Doppler illustrated in FIG. 4, and extra work and error caused by processing high-frequency background Doppler can be reduced.

For S102, referring to FIG. 7, FIG. 9, and FIG. 11 for details, the optical-path shifting device 502 is first in the first position. Light emitted by the light source 100 is split by the light splitting module 200 to obtain a probe light and a reference light. After the probe light is collimated by the collimating mirror 400, the central line of a main light of the probe light extends through the rotation axis 501x of the scanning unit 501. The probe light is reflected by the scanning unit 501 to the optical-path shifting device 502, and exits from the optical-path shifting device 502. Thereafter, the probe light is transmitted by the relay lens 506, reflected by the dichroic mirror 503 to the ophthalmoscope 504, and transmitted by the ophthalmoscope 504 to enter the eye 800. Then the probe light will scan a vessel B in a first direction S1 (illustrated in FIG. 13) and along a Y-axis direction. After, the probe light carries information of the vessel B returns to the light splitting module 200 according to the original path. Referring to FIG. 6, at this moment, the probe light carrying information of the vessel B interferes with the reference light returned from the reference arm module 300 at the light splitting module 200 to obtain a first interference light. A first phase shift signal $\Phi_a$ of the vessel B is obtained after the first interference light is processed by the control system 700. In order to optimize the apparatus, as described above, the collimating mirror 400, the relay lens 506, the dichroic mirror 503, and the ophthalmoscope 504 can be omitted.

For S103, referring to FIG. 8, FIG. 10, and FIG. 12, the optical-path shifting device 502 is in the second position after rotating 180°. Light emitted by the light source 100 is split by the light splitting module 200 to obtain a reference light and a probe light. After the probe light is collimated by the collimating mirror 400, the central line of a main light 50 of the probe light extends through the rotation axis 501x of the scanning unit 501. The probe light is reflected by the scanning unit 501 to the optical-path shifting device 502, and exits from the optical-path shifting device 502. Thereafter, the probe light is transmitted by the relay lens 506, reflected by the dichroic mirror 503 to the ophthalmoscope 504, and transmitted by the ophthalmoscope 504 to enter the eye 800. Then the probe light will scan the vessel B in a second direction (see FIG. 13) and along a Y-axis direction and carry information of the vessel B, and return to the light splitting module 200 according to the original path. Referring to FIG. 6, at this time, the probe light carrying information of the vessel B interferes with the reference light returned from the reference arm module 300 at the light splitting module 200 to obtain a second interference light, and a second phase shift signal $\Phi_b$ of the vessel B is obtained after the second interference light is processed by the control system 700. Similarly, to optimize the apparatus, as described above, the collimating mirror 400, the relay lens 506, the dichroic mirror 503, and the ophthalmoscope 504 can be omitted.

At S104, blood flow of the vessel to be measured is calculated according to the first phase shift signal and the second phase shift signal.

In one embodiment of the disclosure, blood flow rate of the vessel B is obtained with Formula (1) according to the first phase shift signal $\Phi_a$ measured by the probe light when the optical-path shifting device 502 is in the first position and the second phase shift signal $\Phi_b$ measured by the probe light when the optical-path shifting device 502 is in the second position.

When taking into account of pulsation of the blood flow, a blood flow rate of the vessel B at any time may be defined as V(y,z,t) expressed as:

$$V(y,z,t) = v_A(y,z)P(t) \qquad (2)$$

and the control system may obtain an average blood flow of the vessel B by integrating in space domain and time domain, the average blood flow of the vessel B can be expressed as follows:

$$\overline{F} = \frac{1}{T} \int \int \int V(y, z, t) dy dz dt \qquad (3)$$
$$= \int \int v_A(y, z) dy dz \cdot \frac{1}{T} \int_0^T P(t) dt$$

where T represents a pulsating period of blood flow, and P(t) represents a pulsating function of blood flow of the vessel.

Blood flow of the vessel B to be measured in the retina of the eye can be calculated based on the Formula (1) to Formula (3). It should be emphasized that blood flow of any single-vessel in the retina of the eye is obtained in accordance with Formula (1) to Formula (3).

It should be understood that the second phase shift signal $\Phi_b$ needs to be modified subsequent to step S103 and prior to step S104, which can be described in detail as follows.

In embodiments of the disclosure, time points of acquiring the first phase shift signal $\Phi_a$ and the second phase shift signal $\Phi_b$ are different, blood flow rates of the vessel B at different times are different due to the pulsation of the vessel B, and thus it is necessary to use the control system 700 to modify the second phase shift signal $\Phi_b$. The process of modifying may include the following.

First, a relationship of the first phase shift signal $\Phi_a$ and the second phase shift signal $\Phi_b$ over time is obtained.

Figure 16:
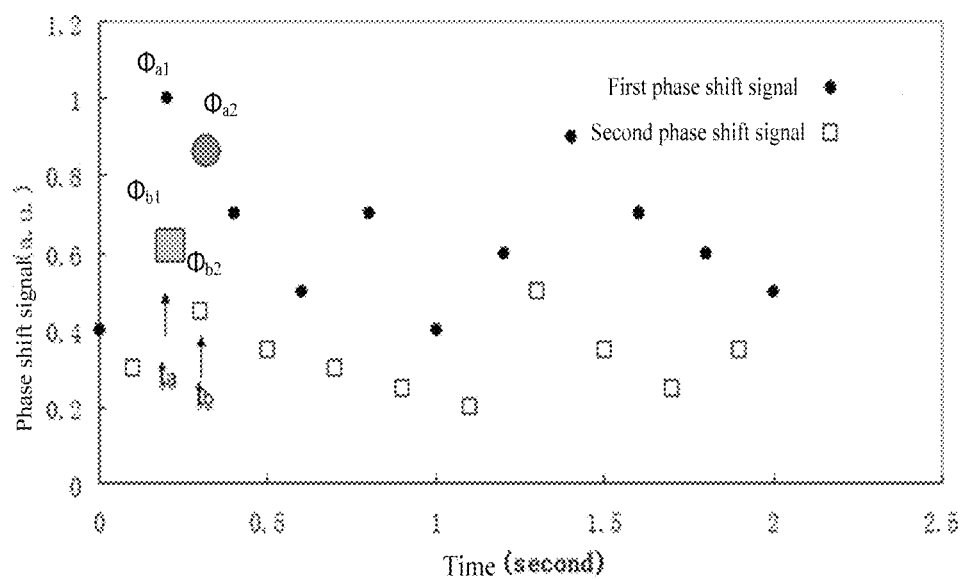
FIG. 16 is a diagram illustrating a relationship of a first phase shift signal and a second phase shift signal over time.

Referring to FIG. 13 and FIG. 16; as illustrated in FIG. 13, when the optical-path shifting device 502 is in the first position and in the second position respectively, the probe light scans the vessel B in the first direction S1 and the second direction S2 alternatively within a predetermined continuous duration of time, e.g., 2 second, so that a time-related phase shift signal distribution diagram is obtained as illustrated in FIG. 16. Black dots represents a plurality of first phase shift signals $\Phi_a$ acquired by the control system 700 at different time points in the first direction S1 when the optical-path shifting device 502 is in the first position; and white box represents a plurality of second phase shift signals $\Phi_b$ measured by the control system 700 at different time points in the second direction S2 when the optical-path shifting device 502 is in the second position.

Then, the second phase shift signal $\Phi_b$ is modified by using interpolation calculation.

In particular, referring to FIG. 16, $\Phi_{a1}$ represents a first phase shift signal obtained by scanning at time $t_a$, and $\Phi_{b2}$ represents a second phase shift signal obtained by scanning at time $t_b$. The control system performs interpolation calculation on the first phase shift signal to obtain a first phase shift signal value $\Phi_{a2}$ at time $t_b$, and then compares the first phase shift signal value $\Phi_{a2}$ at time $t_b$ with the first phase shift signal $\Phi_{a1}$ at time $t_a$ to obtain $k=\Phi_{a1}/\Phi_{a2}$. Similarly, a second phase shift signal $\Phi_{b1}$ at time $t_a$ may be obtained from multiplying k by a second phase shift signal $\Phi_{b2}$ at time $t_b$, the second phase shift signal $\Phi_{b1}$ at time $t_a$ can be given by the relation $\Phi_{b1}=k\Phi_{b2}$.

It should be noted that, prior to performing step S104, the following steps may be implemented. An angle between an axial direction of the vessel and the X-axis direction may be measured. In particular, referring to FIG. 13, when the optical-path shifting device 502 is in the first position, the probe light irradiates into the vessel B of the eye 800 along the first direction S1 and scans the vessel B along the Y-axis direction. When the optical-path shifting device 502 is in the second position after rotating 180°, the probe light irradiates into the vessel B of the eye 800 along the second direction S2 and scans the vessel B along the Y-axis direction. The first direction S1 and the second direction S2 constitute an X-Z plane, and the X-axis direction is parallel to the X axis of the X-Z plane. Therefore, as long as distributions in the space of the vessel B are determined, then an included angle β can be calculated.

Figure 18:
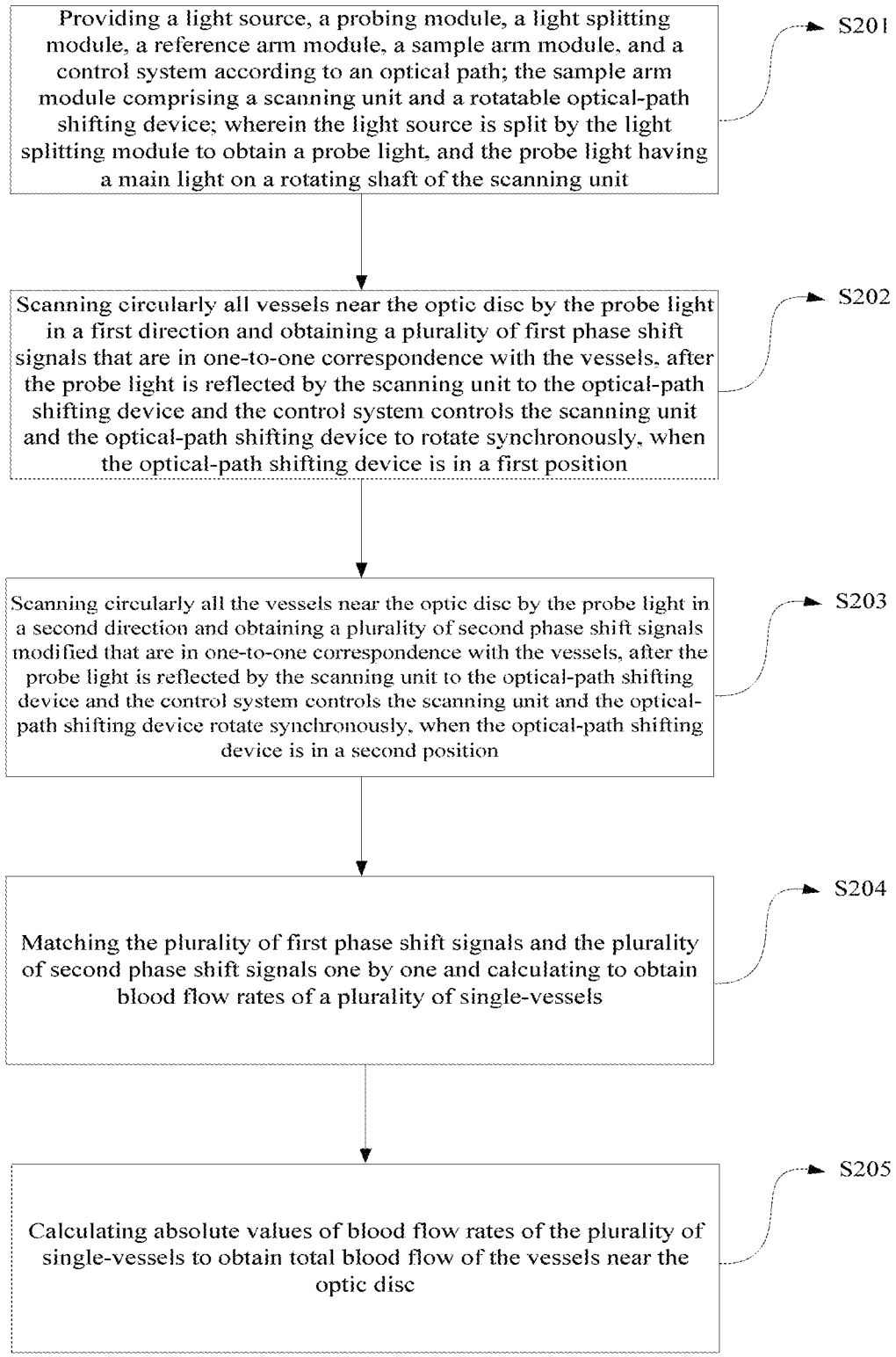
FIG. 18 illustrates a method for measuring blood flow of all vessels near an optic disc with eliminating high-frequency background Doppler.

Referring to FIG. 18, a method for measuring blood flow of all vessels near an optic disc is provided by the disclosure, and the method may include the following steps.

At S201, a light source, a probing module, a light splitting module, a reference arm module, a sample arm module, and a control system are arranged according to an optical-path. The sample arm module includes a scanning unit and a rotatable optical-path shifting device. Light emitted by the light source is split by the light splitting module to obtain a reference light and a probe light, where a central line of a main light of the probe light extends through a rotation axis of the scanning unit.

At S202, when the optical-path shifting device is in a first position, the probe light is configured to be reflected by the scanning unit to the optical-path shifting device, after a computer controls the scanning unit and the optical-path shifting device to rotate synchronously, then the probe light is configured to circularly scan all vessels near the optic disc in a first direction, to obtain a plurality of first phase shift signals that are in one-to-one correspondence with the vessels.

At S203, when the optical-path shifting device is in a second position, the probe light is configured to be reflected by the scanning unit to the optical-path shifting device, after the scanning unit and the optical-path shifting device rotate synchronously under the control of the computer, then the probe light is configured to circularly scan all vessels near the optic disc in a second direction to obtain a plurality of second phase shift signals modified that are in one-to-one correspondence with the vessels.

At S204, the plurality of first phase shift signals and the plurality of second phase shift signals are matched and calculated one by one to obtain multiple blood flow rates of a plurality of single-vessels.

At S205, absolute values of blood flow rates of the plurality of single-vessels are calculated to obtain blood flow of the vessels near the optic disc.

A scanning trajectory when the probe light scans in the second direction is the same as in the first direction; and an angle of rotation is 180° when the optical-path shifting device is rotated from the first position to the second position.

Details of the five steps will be given below.

Figure 14:
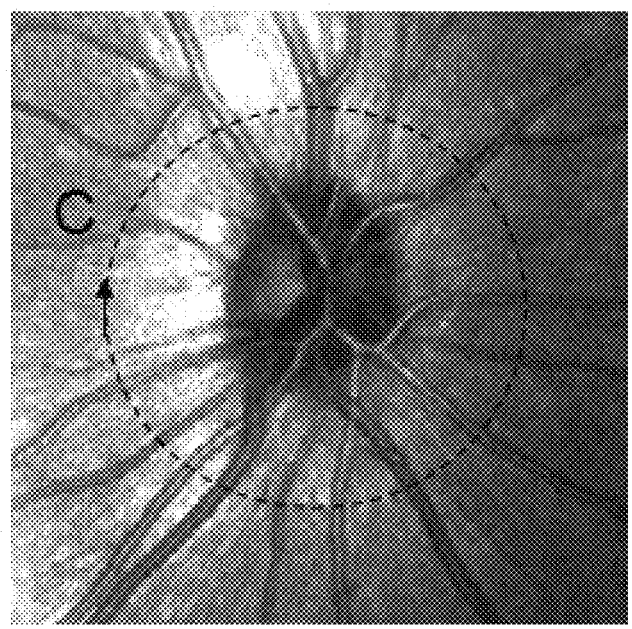
FIG. 14 is a diagram illustrating a scanning trajectory when a probe light scans circularly all vessels in an optic disc.
Figure 15:
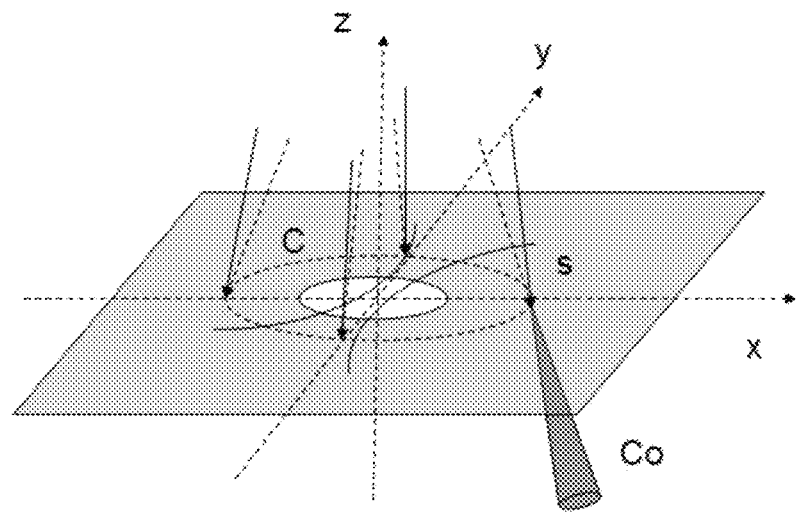
FIG. 15 is a schematic diagram in which a probe light circularly scans all vessels in an optic disc with a same trajectory in a first direction and a second direction respectively.

For step S201, reference is made to the above description of step S101 and will not be repeated here For step S202, when an optical-path shifting device 502 is in a first position as illustrated in FIG. 7, FIG. 9, and FIG. 11, a control system 700 is configured to control the probe light to make a circular scan on a circle C (see FIG. 14) around an optic disc area. FIG. 15 describes how to implement this circular scan. The scanning unit 501 controls the probe light to fall at point S on a circumference (corresponding to the circle C in FIG. 14), at this time, if the scanning unit 501 remains still while the optical-path shifting device 502 is rotated 360°, the probe light will circularly move a conical surface Co. The control system 700 controls the optical-path shifting device 502 and the scanning unit 501 to rotate synchronously, the probe light will scan all vessels around the optic disc circularly (see FIG. 14) along a space vector direction, which is indicated by the first direction S1, that is, the incident direction of the solid line arrow (see FIG. 13). In this way, a plurality of first phase shift signals $\varphi_{a1}$, $\varphi_{a2}$, $\varphi_{a3}$ ... $\varphi_{aN}$ of blood flow of the vessels near the optic disc can be obtained.

For step S203, after the probe light scans circularly for a circle and then returns to point S (see FIG. 15), the optical-path shifting device 502 may switch a phase n quickly (namely is rotated 180°), at this time, the optical-path shifting device 502 is in the second position, and then the probe light will be switched to the second direction S2 along the incident dashed arrow (see FIG. 13). Similar to step S202, after the scanning unit 501 and the optical-path shifting device 502 rotate synchronously under the control of the control system 700, the probe light scans the vessels near the optic disc circularly (see FIG. 14) track along the same circumference scanned when the optical-path shifting device 502 is in the first position, as such, a plurality of second phase shift signals $\varphi_{b1}, \varphi_{b2}, \varphi_{b3} \ldots \varphi_{bN}$ of blood flow of the vessels near the optic disc can be obtained. It should be noted that, the plurality of second phase shift signals $\varphi_{b1}, \varphi_{b2}, \varphi_{b3} \ldots \varphi_{bN}$ also need to be modified in the same manner as the method for measuring blood flow of a single-vessel near the optic disc described above.

For steps S204-S205, the plurality of first phase shift signals $\varphi_{a1}, \varphi_{a2}, \varphi_{a3} \ldots \varphi_{aN}$ and the plurality of second phase shift signals $\varphi_{b1}, \varphi_{b2}, \varphi_{b3} \ldots \varphi_{bN}$ are paired one by one, "pair" referred to herein may be that $\varphi_{a1}$ and $\varphi_{b1}$ are paired, $\varphi_{a2}$ and $\varphi_{b2}$ are paired, $\varphi_{a3}$ and $\varphi_{b3}$ are paired ... $\varphi_{aN}$ and $\varphi_{bN}$, are paired and so on. In order to measure blood flow of all the vessels near the optic disc in a short time, a certain interval period (e.g., 2 seconds) should be set between two circular scans. After the probe light completes the above two scans, an angle β between an axial direction VB of the vessels in the optic disc and the X-axis direction may be determined with reference to a fundus image. FIG. 13 illustrates an example of an angle β between the axial direction VB of a scanned vessel B and the X-axis direction. In particular, the fundus image may be obtained in various ways, for example, via three-dimension OCT, black and white photography or color photography of fundus, linear scanning imaging, and other technologies. In this way, the angle β between an axial direction of each vessel near the optic disc and the X-axis direction can be determined. At this time, blood flow rate values V1, V2, V3 . . . VN of the plurality of single-vessels can be calculated according to Formula (1). Since the blood flow rate is directional, absolute values of these blood flow rate values such as V1, V2, V3, . . . VN need to be calculated, which will then be substituted into Formula (2) and Formula (3) to obtain total blood flow of the vessels near the optic disc of the eye 800.

What still needs to be explained is, the scanning trajectory of the probe light may be in a same circumference when the probe light makes two circular scans on a circle C around the optic disc area and when the optical-path shifting device 502 is in the first position and in the second position. The difference is that, when the optical-path shifting device 502 is in the first position, the probe light is configured to scan circularly each vessel near the optic disc in the first direction S1; and when the optical-path shifting device 502 is in the second position, the probe light is configured to scan circularly each vessel near the optic disc in the second direction S2. The first direction S1 and the second direction S2 remain unchanged when the probe light scans the vessels circularly, that is, an angle α between the first direction S1 and the second direction S2 in the whole process of circular scanning is unchanged. As such, the blood flow rate values of the plurality of single-vessels near the optic disc calculated with Formula (1) and Formula (2) can be more accurate, and accordingly, the total blood flow of the vessels near the optic disc calculated can be more accurate.

Figure 4:
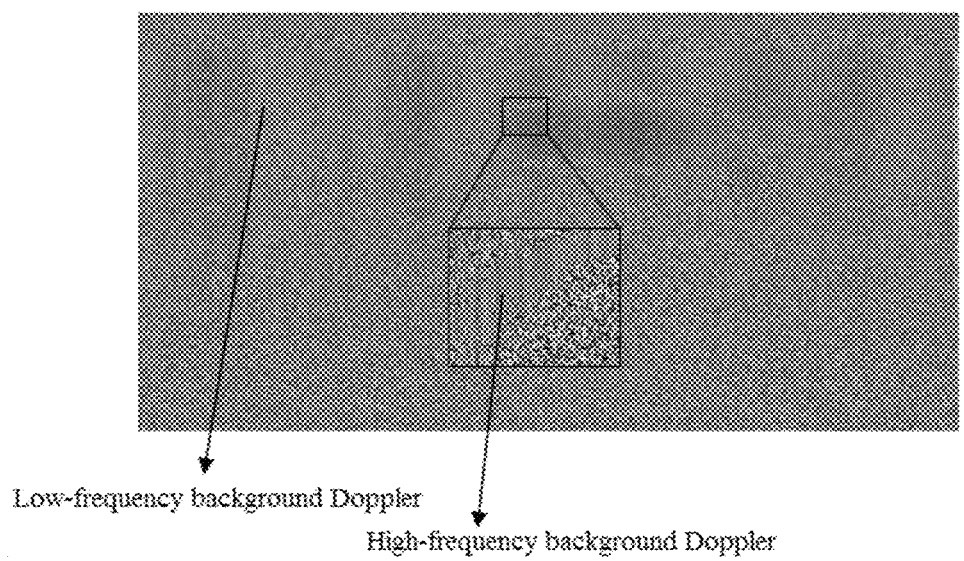
FIG. 4 illustrates an original Doppler image acquired of a vessel B, which has high-frequency background Doppler and low-frequency background Doppler.
Figure 5:
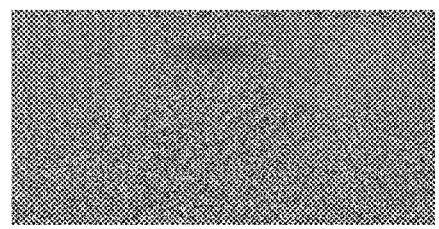
FIG. 5 illustrates an image after high-frequency background Doppler illustrated in FIG. 4 is processed.

In conclusion, with aid of the apparatus and method for measuring blood flow provided in the disclosure, the central line of the main light 50 of the probe light may always extend through the rotation axis 902 of the X-Y galvanometer 900 illustrated in FIG. 1 when the optical path is set, thereby avoiding processing high-frequency background Doppler appearing in the original Doppler image as illustrated in FIG. 4, and the Doppler image with no high-frequency background Doppler illustrated in FIG. 5 can be obtained directly, so that extra work and error caused by processing high-frequency background Doppler can be reduced.

The foregoing description merely depicts some specific embodiments of the disclosure, which however are not intended to limit the disclosure. Any modifications, equivalent substitutions, or improvements made thereto without departing from the spirit and principle of the disclosure shall all be encompassed within the protection of the disclosure.

What is claimed is:

1. An apparatus for measuring blood flow of vessels, comprising:
    a light source, a light splitting module, a reference arm module, a sample arm module, a probing module, and a control system;
    light emitted by the light source being split by the light splitting module to form a reference light and a probe light, the reference light being incident to the reference arm module, and the probe light being incident to the sample arm module; the sample arm module comprising a scanning unit and a rotatable optical-path shifting device, the rotatable optical-path shifting device being rotatable about a rotation axis, and the probe light having a main light on a rotating, a central line of the main light extending through a rotation axis of the scanning unit;
    when the optical-path shifting device is rotated to be in a first position, the probe light being configured to be reflected by the scanning unit to enter the optical-path shifting device, to scan a vessel in a first direction and carry information of the vessel scanned after passing through the optical-path shifting device, to be returned by the sample arm module, and to interfere with the reference light returned from the reference arm module at the light splitting module to generate a first interference light; the first interference light being configured to be probed by the probing module and processed by the control system to obtain a first phase shift signal of the vessel; and
    when the optical-path shifting device is rotated to be in a second position, the probe light being configured to be reflected by the scanning unit to enter the optical-path shifting device to scan the vessel in a second direction and carry information of the vessel scanned after passing through the optical-path shifting device, to be returned by the sample arm module, and to interfere with the reference light returned from the reference arm module at the light splitting module to generate a second interference light; the second interference light being configured to be probed by the probing module and processed by the control system to obtain a second phase shift signal of the vessel;
    wherein a line extending through a point where the main light of the probe light irradiates on the scanning unit and a point where the main light of the probe light irradiates on the optical-path shifting device is collinear with the rotation axis of the optical-path shifting device.

2. The apparatus of claim 1, wherein when the optical-path shifting device is rotated to the second position from the first position, an angle of rotation is 180°.

3. The apparatus of claim 2, wherein the sample arm module further comprises a collimating mirror, a relay lens, a dichroic mirror, and a ophthalmoscope; the collimating mirror being configured to collimate the probe light obtained after splitting by the light splitting module; the relay lens being configured to converge the probe light from the optical-path shifting device on the dichroic mirror; the dichroic mirror being configured to reflect the probe light from the relay lens to the ophthalmoscope to be converged to scan the vessels.

4. The apparatus of claim 2, wherein the scanning unit is an X-Y galvanometer, and the rotation axis of the scanning unit is a rotation axis of the X-Y galvanometer.

5. The apparatus of claim 2, wherein the optical-path shifting device is at least one of a plate glass having two chamfered ends, two speculums arranged in parallel, or a prism.

6. The apparatus of claim 1, wherein the sample arm module further comprises a collimating mirror, a relay lens, a dichroic mirror, and a ophthalmoscope; the collimating mirror being configured to collimate the probe light obtained after splitting by the light splitting module; the relay lens being configured to converge the probe light from the optical-path shifting device on the dichroic mirror; the dichroic mirror being configured to reflect the probe light from the relay lens to the ophthalmoscope to be converged to scan the vessels.

7. The apparatus of claim 6, wherein the sample arm module further comprises a preview module, the preview module comprises an illumination light source, a first lens, and a camera; wherein the light emitted by the illumination light source irradiates into eyes and reflects in fundus, then the light reflected is transmitted sequentially by the ophthalmoscope, the dichroic mirror, and the first lens, and then is received by the camera and displayed by a computer.

8. The apparatus of claim 1, wherein the scanning unit is an X-Y galvanometer, and the rotation axis of the scanning unit is a rotation axis of the X-Y galvanometer.

9. The apparatus of claim 1, wherein the optical-path shifting device is at least one of a plate glass having two chamfered ends, two speculums arranged in parallel, or a prism.

10. A method for measuring blood flow of a single-vessel, comprising:
providing a light source, a probing module, a light splitting module, a reference arm module, a sample arm module, and a control system according to an optical path; the sample arm module comprising a scanning unit and a rotatable optical-path shifting device, the rotatable optical-path shifting device being rotatable about a rotation axis, and a central line of a main light of a probe light of the light source obtained by the light splitting module extending through a rotation axis of the scanning unit;
scanning a vessel in a first direction by the probe light and generating a first phase shift signal, after the probe light is reflected by the scanning unit and entering and passing through the optical-path shifting device when the optical-path shifting device is rotated to be in a first position;
scanning the vessel in a second direction by the probe light and generating a second phase shift signal, after the probe light be reflected by the scanning unit and entering and passing through the optical-path shifting device when the optical-path shifting device is rotated to be in a second position, wherein a line extending through a point where the main light of the probe light irradiates on the scanning unit and a point where the main light of the probe light irradiates on the optical-path shifting device is collinear with the rotation axis of the optical-path shifting device; and
calculating blood flow of the vessel according to the first phase shift signal and the second phase shift signal.

11. The method of claim 10, wherein after scanning the vessel in the second direction by the probe light and generating the second phase shift signal, the method further comprises:
modifying the second phase shift signal, comprising:
obtaining a relationship of the first phase shift signal and the second phase shift signal over time; and
modifying the second phase shift signal by using interpolation calculation.

12. The method of claim 10, wherein prior to calculating the blood flow of the vessel according to the first phase shift signal and the second phase shift signal, the method further comprises:
measuring an angle between an axial direction of the vessel and an X-axis direction;
wherein the probe light is configured to scan the vessel in the first direction when the optical-path shifting device is in the first position, and the probe light is configured to scan the vessel in the second direction when the optical-path shifting device is in the second position;
wherein the first direction and the second direction constitute an X-Z plane.

13. A method for measuring total blood flow of vessels near an optic disc, comprising:
providing a light source, a probing module, a light splitting module, a reference arm module, a sample arm module, and a control system according to an optical path; the sample arm module comprising a scanning unit and a rotatable optical-path shifting device, the rotatable optical-path shifting device being rotatable about a rotation axis; wherein the light source is split by the light splitting module to obtain a probe light, and the probe light having a main light on a, and a central line of the main light extending through a rotation axis of the scanning unit;
scanning circularly all vessels near the optic disc by the probe light in a first direction and obtaining a plurality of first phase shift signals that are in one-to-one correspondence with the vessels, after the probe light is reflected by the scanning unit to the optical-path shifting device and the control system controls the scanning unit and the optical-path shifting device to rotate synchronously when the optical-path shifting device is rotated to be in a first position;
scanning circularly all the vessels near the optic disc by the probe light in a second direction and obtaining a plurality of second phase shift signals modified that are in one-to-one correspondence with the vessels, after the probe light is reflected by the scanning unit to the optical-path shifting device and the control system controls the scanning unit and the optical-path shifting device rotate synchronously when the optical-path shifting device is rotated to be in a second position, wherein a line extending through a point where the main light of the probe light irradiates on the scanning unit and a point where the main light of the probe light irradiates on the optical-path shifting device is collinear with the rotation axis of the optical-path shifting device;
matching the plurality of first phase shift signals and the plurality of second phase shift signals one by one and calculating to obtain blood flow rates of a plurality of single-vessels; and
calculating absolute values of blood flow rates of the plurality of single-vessels to obtain total blood flow of the vessels near the optic disc;

wherein a scanning trajectory of the probe light in the second direction is the same as in the first direction.

* * * * *